United States Patent [19]

Mettler et al.

[11] Patent Number: 4,956,473

[45] Date of Patent: Sep. 11, 1990

[54] 2-AZA-4-(ALKOXYCARBONYL)-SPIRO[4,5]DECAN-3-ONE

[75] Inventors: Hans P. Mettler, Brig-Glis; Gareth Griffiths, Visp; Lester Mills, Naters; Felix Previdoli, Brig, all of Switzerland

[73] Assignee: Lonza Ltd., Gampel, Switzerland

[21] Appl. No.: 400,820

[22] Filed: Aug. 30, 1989

[30] Foreign Application Priority Data

Sep. 1, 1988 [CH] Switzerland ............... 3272/88
Apr. 12, 1989 [CH] Switzerland ............... 1382/89
Apr. 12, 1989 [CH] Switzerland ............... 1383/89

[51] Int. Cl.$^5$ ............... C07D 209/54; C07C 255/46; C07B 43/06
[52] U.S. Cl. ............... 548/408; 558/431
[58] Field of Search ............... 548/408

[56] References Cited

U.S. PATENT DOCUMENTS 4,024,175  5/1977  Satzinger et al. ............... 424/319
4,152,326  5/1979  Harterstein et al. ............... 546/16
4,855,444  8/1989  Wambach ............... 548/408

FOREIGN PATENT DOCUMENTS 1350582  4/1974  United Kingdom.

OTHER PUBLICATIONS

*Drugs of the Future*, vol. 9, No. 6 (1984), pp 418 and 419.

Koelsch et al., JACS, vol. 66 (Nov. 1944), pp. 1883 & 1884.
Banerjee et al., J. Indian Chem. Soc., vol. LI (Jan. 1974), pp. 67–72.
Kemp et al., "Organic Chemistry" (1980), p. 38.

*Primary Examiner*—Mark L. Berch
*Attorney, Agent, or Firm*—Fisher, Christen & Sabol

[57] ABSTRACT

2-Aza-4-(alkoxycarbonyl)spiro[4,5]-decan-3-one and a process for the production of it, starting either from cyclohexylidene malonic acid esters or cyclohexylidene cyanoalkylates. The cyclohexylidene malonic acid ester is reacted with hydrocyanic acid in the presence of a catalytic amount of alkali cyanide or with a stoichiometric amount of alkali cyanide, in an alcohol, and subsequently treated with an acid. The resultant (1-cyanocyclohexyl) malonic acid dialkyl ester is converted by catalytic hydrogenation into the product. The cyclohexylidene cyanoalkylate is reacted with a stoichiometric amount of alkali cyanide, in an alcohol or with hydrocyanic acid in the presence of a catalytic amount of an alkali cyanide. The resultant (1-cyanocyclohexyl)-cyanoacetic acid alkyl ester is reacted in an alcohol in an acid to provide (1-cyanocyclohexyl) malonic acid dialkyl ester. The later ester is converted by catalytic hydrogenation into the product. Process of using the product for the production of 1-(aminomethyl)cyclohexane acetic acid by converting the product with HCl or sulfuric acid at an elevated temperature.

3 Claims, No Drawings

2-AZA-4-(ALKOXYCARBONYL)SPIRO[4,5]DECAN-3-ONE

BACKGROUND OF THE INVENTION

1. Field Of the Invention

The invention relates to 2-aza-4-(alkoxycarbonyl) spiro[4,5]decan-3-ones and a process for their production. 2-Aza-4-(alkoxycarbonyl)-spiro[4,5]decan-3-ones are valuable starting products for the production of the anticonvulsive agent Gabapentin [1-(aminomethyl)cyclohexaneacetic acid].

2. Background Art

Gabapentin, as well as its production, are described in *Drugs Of The Future,* Vol. 9, no. 6, (1984), pp. 418–419, as well as in U.S. Pat. Nos. 4,024,175 and 4,152,326. The process described therein proceeds by seven to eight steps and is relatively expensive.

BROAD DESCRIPTION OF THE INVENTION

The main object of the invention is to make new products available, which are suitable, in a simple way for obtaining 1-(aminomethyl)cyclohexaneacetic acid. Other objects and advantages of the invention are set out herein or are obvious herefrom to one skilled in the art.

The objects and advantages of the invention are achieved by products and processes of the invention.

The invention involves 2-aza-4-(alkoxycarbonyl) spiro[4,5]-decan-3-ones of the formula:

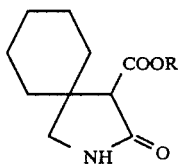

(1)

wherein R is a lower alkyl radical of 1 to 4 C atoms, which preferably is 2-aza-4-(methoxycarbonyl)-spiro[4,5]-decan-3-one or 2-aza-4-(ethoxycarbonyl)-spiro[4,5]-decan-3-one. The invention also involves (1-cyanocyclohexyl)malonic acid dialkyl esters of the formula:

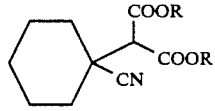

(3)

wherein R is a lower alkyl radical of 1 to 4 C atoms, which preferably is (1-cyanocyclohexyl)malonic acid dimethyl ester or (1-cyanocyclohexyl)malonic acid diethyl ester.

The invention further involves the process for the production of 2-aza-4-(alkoxycarbonyl)spiro[4,5]-decan-3-ones. In this first embodiment of the invention process, cyclohexylidene malonic acid alkyl ester of the formula:

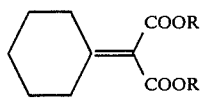

(2)

wherein R is a lower alkyl of 1 to 4 C atoms, is reacted in a first step either with hydrocyanic acid, in the presence of a catalytic amount of alkali cyanide or with a stoichiometric amount of alkali cyanide, in an alcohol, and subsequently treated with an acid, into the corresponding (1-cyanocyclohexyl)malonic acid dialkyl ester of the formula:

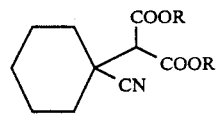

(3)

wherein R is defined as above. The latter ester of formula (3), in a second step, is converted by catalytic hydrogenation into the 2-aza-4-(alkoxycarbonyl)-spiro[4,5]-decan-3-one.

Preferably the reaction in the first step is performed either at a temperature of 20° to 150° C. and under pressure adjusting itself at the reaction temperature with HCN in an amount of 1 to 20 equivalents, relative to the starting product according to formula (2), and in the presence of an alkali cyanide in an amount of 0.1 to 50 mol percent, relative to the starting product according to formula (2), or refluxed with an amount of 1 to 5 equivalents of an alkali cyanide, relative to the starting product according to formula (2), in an alcohol. Preferably the catalytic hydrogenation in the second step is performed at a temperature of 20° to 150° C. and an $H_2$ pressure of 1 to 100 bars.

The invention also involves the process for the production of 2-aza-4-(alkoxycarbonyl)spiro[4,5]-decan-3-ones. In this second embodiment of the invention process, a cyclohexylidene cyanoalkylate of the formula:

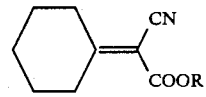

(4)

wherein R is defined as above, in a first step is reacted either with a stoichiometric amount of alkali cyanide, in an alcohol, or with hydrocyanic acid, in the presence of a catalytic amount of an alkali cyanide into the corresponding (1-cyanocyclohexyl)-cyanoacetic acid alkyl ester of the formula:

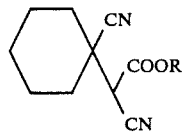

(5)

wherein R is defined as above, in a second step the latter is reacted in an alcohol with an acid, into the corresponding (1-cyanocyclohexyl)malonic acid dialkyl ester of the formula:

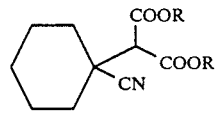

(3)

wherein R is defined as above, and the latter is converted in a third step into the 2-aza-4-(alkoxycarbonyl)-spiro[4,5]-decan-3-one by catalytic hydrogenation.

Preferably the reaction is performed in a first step either with an amount of 1 to 5 equivalents of alkali cyanide, relative to the starting product according to formula (4), in a refluxed alcohol, or at a temperature of 20° to 150° C. and a pressure adjusting itself at the reaction temperature with HCN in an amount of 1 to 20 equivalents, relative to the starting product according to formula (4), and in the presence of alkali cyanide in an amount of 0.1 to 50 mol percent, relative to the starting product according to formula (4). Preferably the reaction is performed in a second step at a temperature of $-20°$ to 50° C. and under a pressure of 1 to 10 bars with 1 to 100 equivalents of an acid, relative to the starting product according to formula (5), in an alcohol. Preferably the catalytic hydrogenation is performed in the third step at a temperature of 20° to 150° C. and an $H_2$ pressure of 1 to 100 bars.

The invention also includes the use of a 2-aza-4-(alkoxycarbonyl)spiro[4,5]-decan-3-one for the production of 1-(aminomethyl)cyclohexaneacetic acid.

DETAILED DESCRIPTION OF THE INVENTION

The following deals with the first embodiment of the invention process:

The starting product of formula (2) used for the process of the invention can be produced in a simple and known way by a Knoevenagel condensation reaction from cyclohexanone and alkyl malonate.

The cyclohexylidene malonic acid alkyl ester of formula (2) thus-produced is converted in a first step either with hydrocyanic acid, in the presence of catalytic amounts of an alkali cyanide, or with a stoichiometric amount of alkali cyanide, in an alcohol, and with the subsequent addition of an acid, into a (1-cyanocyclohexyl)malonic acid dialkyl ester of formula (3). The amount of HCN is 1 to 20 equivalents, preferably 3 to 5 equivalents, relative to the starting product of formula (2). The amount of alkali cyanide is 0.1 to 50 mol percent, preferably 10 to 20 mol percent, relative to starting product of formula (2). Sodium or potassium cyanide can be used as the alkali cyanide; preferably potassium cyanide is used.

The reaction can be performed without a solvent or with a solvent. Lower alcohols, such as, methanol, ethanol, propanol and butanol, lower alcohol/water mixtures, esters with lower alcohols in the ester group, such as, ethyl acetate, methyl acetate and propyl acetate, and ketones, such as, acetone and methyl ethyl ketone, can be used as solvents. Preferably the reaction is performed without solvent.

The reaction in the first step is performed at a temperature of 20° to 150° C., preferably at 90° to 120° C., and preferably a closed vessel (autoclave) is used and in each case the pressure, given by the reaction temperature, is adjusted.

The amount of alkali cyanide (for the second process alternative) is 1 to 5 equivalents, preferably 1 to 1.5 equivalents, relative to starting product of formula (2), if the pH of the mixture is kept at a value of 10.0 to 13.0 by continuous addition of acid/alcohol. Sodium or potassium cyanide can be used as the alkali cyanide; preferably potassium cyanide is used.

Mineral acids, such as, hydrochloric acid or sulfuric acid, or organic acids, such as, formic acid or acetic acid, can be used as the acid; preferably hydrochloric acid is used.

Lower alcohols, such as, methanol, ethanol, propanol and butanol, or lower alcohol/water mixtures can be used as the solvent. Preferably the reaction is performed with the alcohol corresponding to the alkyl ester group.

The reaction temperature is 0° C. to reflux temperature, preferably at reflux temperature.

The (1-cyanocyclohexyl)malonic acid dialkyl ester of formula (3) formed after the first step is converted in second step by catalytic hydrogenation into the 2-aza-4-(alkoxycarbonyl)spiro[4,5]-decan-3-one.

Raney nickel, Raney cobalt or noble metal catalysts, such as, platinum, palladium, rhodium or ruthenium on supports such as, carbon, can be used as the catalyst. The amount of the catalyst, with the preferred use of Raney nickel, is suitably 1 to 50 percent by weight, relative to the starting product of formula (3). Lower alcohols, such as, ethanol or other polar solvents, such as, ester and ether, are used as the solvent. The reaction temperature is 20° to 150°, preferably 80° to 100° C. The $H_2$ pressure that can be used is 1 to 100 bars, preferably 5 to 10 bars.

The following deals with the second embodiment of the invention process:

The starting product of formula (4) used for the process of the invention can also be produced in a simple and known way by Knoevenagel condensation reaction from cyclohexanone and cyanoalkylate.

The cyclohexylidene cyanoalkylate of formula (4) thus-produced is converted in the first step either with hydrocyanic acid, in the presence of catalytic amounts of an alkali cyanide, or with a stoichiometric amount of alkali cyanide, in an alcohol, into the (1-cyanocyclohexyl) cyanoacetic acid alkyl ester of formula (5). The amount of HCN is 1 to 20 equivalents, preferably 3 to 5 equivalents, relative to the starting product of formula (2). The amount of the alkali cyanide is 0.1 to 50 mol percent, preferably 10 to 20 mol percent, relative to starting product of formula (2). Sodium or potassium cyanide can be used as the alkali cyanide; preferably potassium cyanide is used.

The reaction can be performed without a solvent or with a solvent. Lower alcohols, such as, methanol, ethanol, propanol and butanol, lower alcohol/water mixtures, esters with lower alcohols in the ester group, such as, ethyl acetate, methyl acetate and propyl acetate, and ketones, such as, acetone and methyl ethyl ketone, can be used as the solvents. Preferably the reaction is performed without a solvent.

The reaction in the first step is performed at a temperature of 20° to 150° C., preferably at 90° to 120° C., and preferably a closed vessel (autoclave) is used and in each case the pressure, given by the reaction temperature, is adjusted.

The amount of the alkali cyanide (for the second process alternative) is 1 to 5 equivalents, preferably 1 to 1.5 equivalents, relative to the starting product of formula (4).

Lower alcohols, such as, methanol, ethanol, propanol and butanol can be used as the solvent. Preferably the reaction is performed with the alcohol corresponding to the alkyl ester group.

The (1-cyanocyclohexyl)cyanoacetic acid alkyl ester of formula (5) formed in the first step is converted in the second step, preferably in a closed vessel, with 1 to 100 equivalents of an acid, preferably with 10 to 20 equivalents relative to starting product of formula (5), at a temperature of −20° to 50° C. and a pressure of 1 to 10 bars, preferably at 0° to 20° C. and a pressure of 2 to 3 bars, into the (1-cyanocyclohexyl)malonic acid dialkyl ester of formula (6).

Mineral acids, such as, hydrochloric acid and sulfuric acid, as well as organic acids, such as, formic acid and acetic acid, can be used as acids; preferably hydrochloric acid is used.

The lower alcohols corresponding to the alkyl ester group, alone or in combination with an ether, a hydrocarbon, for example, toluene and hexane, or a halogenated hydrocarbon, for example, methylene chloride, are used as the solvent. Preferably the reaction to ethyl ester is performed with ethanol.

The (1-cyanocyclohexyl)malonic acid dialkyl ester of formula (6) formed in the second step is converted in the third step by catalytic hydrogenation into the 2-aza-4-(alkoxycarbonyl)spiro[4,5]-decan-3-one.

Raney nickel, Raney cobalt or noble metal catalysts, such as, platinum, palladium, rhodium and ruthenium on supports, such as, carbon, can be used as the catalyst. The amount of the catalyst, with the preferred use of Raney nickel, is suitably 1 to 50 percent by weight, relative to the starting product of formula (6). Lower alcohols, such as, ethanol, or other polar solvents, such as ester or ether, are used as the solvent.

The reaction temperature is 20° to 150° C., preferably 80° to 100° C. The $H_2$ pressure that can be used is 1 to 100 bars, preferably 5 to 10 bars.

The new 2-aza-4-(alkoxycarbonyl)spiro[4,5]-decan-3-ones can be converted by hydrolysis with HCl or sulfuric acid at an increased temperature of about 50° to 220° C. into the corresponding Gabapentin salt. If HCl is used, e.g., as 20 percent solution in water, the corresponding Gabapentin hydrochloride results. The hydrochloride can be removed in a known manner to provide the free compound.

EXAMPLE 1

Cyclohexylidene malonic acid diemethyl ester (not according to the invention)

A solution of titanium tetrachloride (95.1 g, 0.5 mol) in carbon tetrachloride (125 ml) was added to tetrahydrofuran (1000 ml) at about 0° C. under nitrogen in 65 minutes. Then a mixture of cyclohexanone (24.6 g, 0.25 mol) and malonic acid dimethyl ester (33.0 g, 0.25 mol) was added at 0° C. in 15 minutes. Pyridine (79.0 g, 1.0 mol) in THF 175 ml) was added to the yellow suspension in 60 minutes and the mixture was stirred for another 18 hours at room temperature. Water (250 ml) was added and the two phases were separated. The aqueous phase was extracted twice with 90 ml of ethyl acetate each and the combined organic phases were washed with saturated sodium chloride and saturated sodium carbonate solution (100 ml each), dried with magnesium sulfate, filtered and concentrated by evaporation. Distillation (81° to 83° C./1 mbar) yielded 22.5 g of product, corresponding to 43 percent yield (relative to malonate used).

EXAMPLE 2

(1-Cyanocyclohexyl)malonic acid dimethyl ester

A mixture of cyclohexylidene malonic acid dimethyl ester (21.5 g, 94 mmol), hydrocyanic acid (19 ml, 485 mmol) and potassium cyanide (0.92 g, 14 mmol) was heated in an autoclave for 6 hours to 120° C. After cooling to room temperature, the excess hydrocyanic acid was driven off with nitrogen. The raw product was dissolved in ethyl acetate and filtered. The filtrate (24.2 g), concentrated by evaporation, was recrystallized from ethanol and yielded 15.5 g of product, corresponding to a yield of 69 percent (relative to malonate used). Data for the product was:
Melting point: 74° to 75° C.

| $^1$H-NMR: (CDCl$_3$, 300 MHz) δ | |
|---|---|
| 1.0–2.3 | (m, 10 H) |
| 3.47 | (s, 1 H) |
| 3.81 | (s, 6 H) |

Elementary analysis for $C_{12}H_{17}NO_4$ (239.3):
Cld.: C 60.2%; H 7.2%; N 5.9%.
Fnd: C 60.6%; H 7.3%; N 6.5%.

EXAMPLE 3

2-Aza-4-(methoxycarbonyl)spiro[4,5]-decan-3-one (1)

A solution of (1-cyanocyclohexyl)malonic acid dimethyl ester (7.50 g, 29 mmol) in ethanol (150 ml) was hydrogenated at 10 bars of hydrogen pressure and 90° C. on 3.00 g of Raney nickel for 4.5 hours. The reaction mixture was filtered, the filtrate was concentrated by evaporation and dried. The residue was mixed with 5 g of hot toluene, inoculated with some product crystals and allowed to stand for 4 hours at 4° C. The formed crystals were filtered off, washed with toluene and dried. 4.13 g of product corresponding to a yield of 66 percent (relative to malonate used) was obtained. Data for the product was:
Melting point: 73° to 75° C.

| $^1$H-NMR: (CDCl$_3$, 300 MHz) δ | |
|---|---|
| 1.28–1.71 | (m, 10 H) |
| 3.10 | (s, 1 H) |
| 3.20 | (d, J = 10Hz, 1 H) |
| 3.36 | (d, J = 10Hz, 1 H) |
| 3.78 | (s, 3 H) |
| 6.89 | (3, 1 H) |

Elementary analysis $C_{11}H_{17}NO_3$ (211.3):
Cld.: C 62.5%; H 8.1%; N 6.6%.
Fnd: C 62.9%; H 8.3%; N 7.2%.

EXAMPLES 4 AND 5

The corresponding (1-cyanocyclohexyl)malonic acid diethyl ester and the 2-aza-4-(ethoxycarbonyl)-spiro[4,5]-decan-3-one are produced according to Examples 1 to 3. The yields correspond to those mentioned in Examples 1 to 3.

(1-Cyanocyclohexyl)malonic acid diethyl ester (Example 4)

Data for the product was:
Melting point: 90° to 92° C.

| $^1$H-NMR: (CDCl$_3$, 300 MHz) δ | |
|---|---|
| 1.30 | (t, J = 7.2 Hz, 6 H) |
| 1.15–2.23 | (m, 10 H) |
| 3.40 | (s, 1 H) |
| 4.20–4.35 | (m, 4 H) |

Elementary analysis for $C_{14}H_{21}NO_4$ (267.3)
Cld.: C 62.9; H 7.9; N 5.2.
Fnd: C 62.9; H 7.9; N 5.5.

2-Aza-4-(ethoxycarbonyl)spiro[4,5]-decan-3-one
(Example 5)

Data for the product was:
Melting point: 72.° to 74° C.

| $^1$H-NMR: (CDCl$_3$, 300 MHz) δ | |
|---|---|
| 1.29 | (t, J = 7.2 Hz, 3 H) |
| 1.25–1.68 | (m, 10 H) |
| 3.06 | (s, 1 H) |
| 3.18 | (dxd, J$_1$ = 9.5 Hz, J$_2$ = 1.1 Hz, 1 H) |
| 3.34 | (d, J = 9.5 Hz, 1 H) |
| 4.21 | (q, J = 7.1 Hz, 2 H) |
| 6.92 | (s, 1 H) |

Elementary analysis for C$_{12}$H$_{19}$NO$_3$ (225.3):
Cld.: C 64.0; H 8.5; N 6.2.
Fnd: C 63.6; H 8.6; N 6.4.

EXAMPLE 6

(1-Cyanocyclohexyl)malonic acid diethyl ester

A mixture of potassium cyanide (18.1 g, 0.27 mol) and cyclohexylidene malonic acid diethyl ester (44.0 g, 0.18 mol) in ethanol (180 ml) was refluxed, and the pH of the mixture was kept at a value of 10.5 to 11.5 by continuous addition of HCl/ethanol. After a reaction time of 16 hours, it was cooled to 30° C. and a pH of about 5 was adjusted by the addition of HCl/EtOH (24 percent, about 14 g, 0.1 mol). The precipitated potassium chloride was filtered off and washed with ethanol (200 ml). The filtrate, concentrated by evaporation, was recrystallized from ethanol and yielded a total of 42.1 g of product, corresponding to a yield of 88 percent, relative to the cyclohexylidene malonic acid ethyl ester used.

EXAMPLE 7

Cyclohexylidene cyanoacetate (not according to the invention)

A solution of cyclohexanone (58.9 g, 0.6 mol), cyanoacetic acid ethyl ester (3.8 g, 0.5 mol), ammonium acetate (3.8 g, 0.05 mol) and acetic acid (6.0 g, 0.1 mol) was refluxed in toluene (50 ml). Then 18 g of the aqueous phase was separated on the water separator within 6 hours. The organic solution was washed three times with water (100 ml each) and distilled in a vacuum. The distillation (111° to 115° C./0.3 mbar) yielded 71.4 g of product, corresponding to 74 percent yield (relative to the cyanoacetic acid ethyl ester used).

EXAMPLE 8

(1-cyanocyclohexyl) cyanoacetic acid ethyl ester

A suspension of potassium cyanide (33.0 g, 0.5 mol) in ethanol (400 ml) was refluxed and then mixed with cyclohexylidene cyanoacetate (103.3 g, 0.5 mol). After a reaction time of 45 minutes, it was cooled to 60° C. and a pH of about 5 was adjusted by introduction of HCl gas (about 18 g, 0.5 mol). The precipitated potassium chloride was filtered off and washed with ethanol (200 ml). The filtrate, concentrated by evaporation, was recrystallized from ethanol and yielded a total of 99.6 g of product, corresponding to a yield of 94 percent (relative to the cyclohexylidene cyanoacetate used).

EXAMPLE 9

(1-Cyanocyclohexyl)malonic acid diethyl ester

A mixture of (1-cyanocyclohexyl)cyanoacetic acid ethyl ester (2.50 g, 11.3 mmol) in ethanol (100 ml) was saturated in a autoclave with HCl gas, about 11 g, 0.3 mol, at 0° C. After a reaction time of 16 hours at 0° C./2 bars, the mixture was concentrated by evaporation in a rotation evaporator, mixed with ethanol (3 ml) and water (10 ml) and then stirred for 4 hours at 0° C. 2.37 g of the product, corresponding to a yield of 75 percent (relative to the (1-cyanocyclohexyl)cyanoacetic acid ethyl ester used) was isolated by filtration. Data for the product was:

Melting point: 90° to 92° C.

EXAMPLE 10

(1-Cyanocyclohexyl)cyanoacetic acid ethyl ester

Ethyl cyclohexilidene cyanoacetate (19.71 g, 100 mmol) was added to a suspension of potassium cyanide (1.33 g, 20 mmol) in ethanol (100 ml) at 50° C. Hydrocyanic acid (23.1 ml), 84 mmol) was added to the mixture so that the pH remained in the range of 10.5 to 11.5. After 6 hours at 50° C. the mixture was acidified with hydrogen chloride gas (55 mmol). The precipitated potassium chloride was filtered off and washed with ethanol (50 ml). The filtrate was concentrated to 28 g and cooled to 10° C. The formed crystals were filtered off, washed with ethanol and dried. 18.10 g of product was obtained giving a yield of 82% (relative to the cyanoacetate used).

EXAMPLE 11

(1-(Aminomethyl)cyclohexaneacetic acid hydrochloride

A solution of 2-aza-4-(methoxycarbonyl)spiro[4,5]-decan-3-one (1.53 g, 7.2 mmol) in 30 ml of 20 percent hydrochloric acid was stirred with reflux for 24 hours. The reaction solution was cooled, concentrated by evaporation, dissolved in 30 ml of water and concentrated by evaporation once more as well as dried. The resulting oily liquid was suspended in 20 ml of acetone and stirred for 5 minutes. Then the resulting suspension was filtered, the residue was washed with acetone and dried. 894 mg of the product with a melting point of 114° C. was obtained. The filtrate was concentrated by evaporation, the residue was dissolved in 10 ml of 20 percent hydrochloric acid and refluxed for 48 hours. The reaction solution was cooled, concentrated by evaporation, dissolved in 10 ml of water and again concentrated by evaporation, as well as dried. The resultant oily liquid was suspended in 20 ml of acetone and stirred for 5 minutes. Then the resultant suspension was filtered, the residue was washed with acetone and dried. Another 326 mg of product with a melting point of 117° C. was obtained. Data for the product was:

Yield: 81 percent, relative to lactam used (raw product).
Melting point: 114° to 117° C.
Elementary analysis for C$_9$H$_{18}$NO$_2$Cl (207.7):
Analysis: Cld.: C 52.0%; H 8.7%; N 6.7%.
Fnd: C 50.1%; H 8.9%; N 7.0%.
Water content: 4.2 percent

EXAMPLE 12

(1-Cyanocyclohexyl)cyanoacetic acid ethyl ester

A solution of sodium cyanide (0.5 g, 10 mmol) in water (3 ml) was added at 20°–30° C. to a solution of ethyl cyclohexylidene cyanoacetate (2.0 g, 10 mmol) in ethanol (5 ml). After 1 h a gas chromatogram of the reaction mixture (acidified with acetic acid) proved the formation of the product (86 area-% of (1-cyanocyclohexyl)cyanoacetic acid ethyl ester, 5 area of cyclohexlidene cyanoacetate).
What is claimed:
1. 2-Aza-4-(alkoxycarbonyl)spiro[4,5]-decan-3-one of the formula:
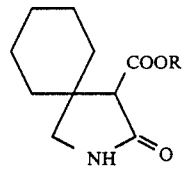
(1)
wherein R is a lower alkyl radical of 1 to 4 C atoms.
2. 2-Aza-4-(methoxycarbonyl)spiro[4,5]-decan-3-one.
3. 2-Aza-4-(ethoxycarbonyl)spiro[4,5]-decan-3-one.
* * * * *